United States Patent [19]

Jani et al.

[11] Patent Number: 5,093,126

[45] Date of Patent: * Mar. 3, 1992

[54] GLAUCOMA FORMULATIONS COMPRISING AN ANIONIC, POLYSULFONIC ACID POLYMER HAVING MUCOMIMETIC PROPERTIES AND A POLYSTYRENE SULFONIC POLYMER

[75] Inventors: Rajni Jani; Yusuf Ali, both of Fort Worth, Tex.

[73] Assignee: Alcon Laboratories, Inc., Fort Worth, Tex.

[*] Notice: The portion of the term of this patent subsequent to Mar. 27, 2007 has been disclaimed.

[21] Appl. No.: 308,164

[22] Filed: Feb. 8, 1989

Related U.S. Application Data

[63] Continuation-in-part of Ser. No. 102,176, Sep. 26, 1987, abandoned, which is a continuation of Ser. No. 800,933, Nov. 22, 1985, abandoned.

[51] Int. Cl.⁵ .......................... A61K 9/00; A61K 9/14; A61F 2/00
[52] U.S. Cl. .................................. 424/428; 424/400; 424/486
[58] Field of Search ............... 424/705, 706, 709, 428, 424/400, 486

[56] References Cited

U.S. PATENT DOCUMENTS

| | | | |
|---|---|---|---|
| 3,867,519 | 2/1975 | Michaels | 424/19 |
| 3,962,414 | 6/1976 | Michaels | 424/19 |
| 3,987,163 | 10/1976 | Rankin | 424/78 |
| 4,127,674 | 11/1978 | Leopold | 424/324 |
| 4,128,631 | 12/1978 | Lundmark et al. | 424/70 |
| 4,207,890 | 6/1980 | Mamajek et al. | 128/223 |
| 4,271,143 | 6/1981 | Schoenwald et al. | 424/78 |
| 4,407,792 | 10/1983 | Schoenwald et al. | 424/81 |
| 4,436,730 | 3/1984 | Ellis et al. | 514/915 |
| 4,462,982 | 7/1984 | Samejima et al. | 424/35 |
| 4,521,414 | 6/1985 | Chiou et al. | 524/229 |
| 4,615,882 | 10/1986 | Stockel | 514/840 |
| 4,911,920 | 3/1990 | Jani et al. | 424/81 |

OTHER PUBLICATIONS

Heath et al., "Adsorption of B-Adrenoceptor Antagonists to Amberlite Resin", *British Journal of Clinical Pharmacology*, vol. 15, pp. 490-492 (1983).

Chemical Abstracts, vol. 98, 210936j (1983)-Heath et al.

*Primary Examiner*—Frederick E. Waddell
*Assistant Examiner*—Zohreh A. Fay
*Attorney, Agent, or Firm*—Sally Yeager; Julie Cheng

[57] ABSTRACT

Disclosed are nonstinging, sustained release ophthalmic formulations. The formulations comprise a cationic drug, an acidic mucomimetic polymer and a polystyrene sulfonic acid polymer. In particular, formulations for the control of intraocular pressure and glaucoma are disclosed. Methods for use of the formulations are also disclosed.

14 Claims, No Drawings

GLAUCOMA FORMULATIONS COMPRISING AN ANIONIC, POLYSULFONIC ACID POLYMER HAVING MUCOMIMETIC PROPERTIES AND A POLYSTYRENE SULFONIC POLYMER

This application is a continuation-in-part of Ser. No. 102,176, filed Sept. 29, 1987, now abandoned, which is a continuation of Ser. No. 800,933, filed Nov. 22, 1985, now abandoned.

This invention is directed to ophthalmic formulations. The formulations are characterized as long lasting (sustained release) and are initially and continually comfortable to the eye. In particular, this invention relates to ophthalmic formulations useful in controlling and lowering intraocular pressure (IOP) in the treatment of glaucoma. Specifically, the invention relates to topical ophthalmic formulations of the above characteristics which comprise a basic active in an aqueous solution or gel formed from a combination of an acidic, mucomimetic polymer and a polystyrene sulfonic acid polymer. Such resulting aqueous solution, gel or pourable liquid formulations are characterized by controlled cationic-anionic interactions, which appear to be responsible for the resulting comfort and sustained release properties. This invention also relates to methods of treatment which comprise administering the sustained release, comfortable ophthalmic compositions. In particular, this invention relates to methods of treatment which comprise administering ophthalmic compositions comprising a basic active when indicated for treating ocular hypertension and glaucoma.

The term "basic active" means the active ingredient or ingredients in the disclosed formulations which bear, or are capable of bearing, a positive charge during formulation of the final product or as formulated in the final product form. In addition and in particular, the "basic actives" will also have the desired effect on intraocular pressure. Thus, the term basic, or cationic, active is descriptive for purposes of the disclosure and claims.

Such basic actives include all presently known beta blockers which demonstrate the requisite cationic charge and IOP effect. Typically, such beta blockers are represented by the following generic structure, which structure also represents the beta blocker basic actives of the present disclosure:

$$R^1—O—CH_2—CH(OH)—CH_2—NR^2R^3 \quad [I]$$

wherein: $R^1$ is a substituted or unsubstituted cyclic or aliphatic moiety; cyclic moieties include mono- and polycyclic structures which may contain one or more heteroatoms selected from C, N, and O; $R^2$ and $R^3$ are independently selected from H and substituted and unsubstituted alkyl. With regard to Structure (I), above, the following references are incorporated herein by reference: *Annual Reports in Medicinal Chemistry* 14, 81–87 (1979); *J. Med. Chem.* 1983, 26,1570–1576; ibid., 1984, 27, 503–509; ibid., 1983, 26, 7–11; ibid., 1983, 26, 1561–1569; ibid., 1983, 1109–1112; ibid., 1983, 26, 950–957; ibid., 1983, 26, 649–657; and ibid., 1983, 26, 352–357. Representative of such basic actives are: betaxolol, timolol, befunolol, labetalol, propranolol, bupranolol, metaprolol, bunalol, esmalol, pindolol, carteolol, hepunolol, metipranolol, caliprolol, azotinolol (S-596), diacetolol, acebutolol, salbutamol, atenulol, isoxaprolol, and the like.

The definition of basic active also includes the following classes of drugs which are used in treatment of ocular hypertension and glaucoma: pilocarpine, epinephrine, proepinephrine, norepinephrine, pronorepinephrine, clonidine and clonidine derivatives, for example, p-aminoclonidine and p-acetoamidoclonidine.

Thus, in summary, the basic active component of the present invention is defined by its intraocular pressure lowering effect or static control thereof, and by its cationic nature in an aqueous medium in the pH range of from 3.0 to 8.5. The following patent publications, which are incorporated herein by reference, further representatively demonstrate the basic actives of the present invention: U.S. Pat. Nos. 4,252,984; 3,309,406; 3,619,370; 3,655,663; 3,657,237; 4,012,444; 3,663,607; 3,836,671; 3,857,952; 3,202,660; and 2,774,789.

DETAILED DESCRIPTION OF THE INVENTION

The ophthalmic formulations of the present invention are in the form of: anhydrous salts; pourable, aqueous dispersions; and aqueous solutions or gels. The formulations comprise, in addition to conventional ingredients which provide, for example, bacteriostatic and formulatory balance functions, an acidic mucomimetic polymer, a polystyrene sulfonic acid polymer and the basic active of choice, and may further comprise a cationic resin component to provide further means of sustained drug release. Such anhydrous salt forms are incorporated into ointments or solid ocular inserts which form colloidal gels in situ on administration to the eye. The pourable liquid and aqueous solution and gel embodiments are applied topically to the eye. It should be noted that such liquid, solution and gel embodiments can be obtained from the anhydrous form on formulation with water.

The formulations of the present invention demonstrate sustained release of the basic active and are comfortable on topical administration to the eye. It should be noted, in a general sense, that a stinging sensation results when the basic actives, identified above, are administered neat. Thus, achieving both comfort and sustained release is an unexpected result and permits administration of a class of compounds that otherwise might not be considered.

The acidic mucomimetic polymers, and their salts, useful in the present invention have a molecular weight of from about 50,000 to about 5 million. The polymers are characterized as having sulfonic acid functional groups, and preferably contain from 5 to 20 carbon atoms per functional group.

Suitable acidic mucomimetic polymers useful in the present invention are generally polysulfonic acids and their salts. A specific class of polymers of this description, which is especially preferred, is the polyacrylamidomethyl propane sulfonic acids (and their salts) of the structure:

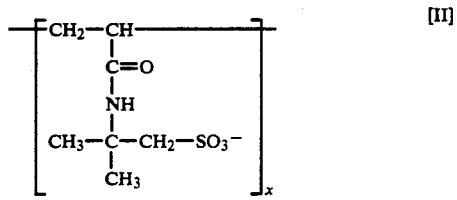

wherein x is an integer permitting a molecular weight range of from about 50,000 to 5,000,000. Such polymers are known; see for example U.S. Pat. No. 4,128,631, which is incorporated herein by reference to the extent that it defines such polymers and how to make them. A representative example of such polysulfonic acids, known as Cosmedia Polymer HSP-1180, is available commercially from Henkel Chemicals.

The acidic mucomimetic polymers are used in the aqueous gel compositions at concentrations between about 10% to 15% by weight; pourable liquid compositions at concentrations of between about 0.05% and 5.0% by weight; and aqueous solutions at concentrations of between about 0.05% to 2.0% by weight.

The polystyrene sulfonic acid polymers (and their salts) which are also used in the formulations of the present invention have the following formula:

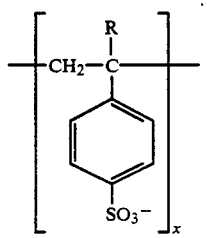

[III]

wherein: R is H or $CH_3$ and X is an integer such that the molecular weight of the polystyrene sulfonic acid polymer may vary from about 10,000 to 1.6 million.

In the preferred polystyrene sulfonic acid of the above formula, R=H and the molecular weight is about 500,000 to 1,000,000, preferably about 600,000. The polystyrene sulfonic acid polymers are used in the formulas of the present invention at a concentration up to about 8.0 wt. %.

The preferred basic actives of the present invention are those disclosed above. The most preferred basic actives are betaxolol and timolol. The basic active, in the aqueous solution, gel and pourable liquid embodiments, is present at a level of from abut 0.01 to 4.0 wt. %; the most preferred range is from 0.10 to 1.0 wt. %.

The present formulations may optionally contain a cationic resin component to provide a still further means of sustained drug release. The cationic resin component of the present formulations not only provide an additional means of sustained release of the basic active, but also appears to enhance both initial and prolonged comfort. Such resins are characterized as either strongly acidic such as those having sulfonic acid functionality, or weakly acidic cation exchangers such as those having carboxylic acid functionality. The resins are incorporated as finely divided powders, that is, 95% of the resulting spheroidal particles have a diameter less than 20.0 microns. While not wishing to be bound by any theory, the sustained release function of the cationic resin is believed to be due to ionic interactions between the resins and the basic actives. These interactions involve binding between drug molecules and the resin to form resinates.

Any pharmaceutical grade cationic ion exchange resin is suitable for the formulation, and they can be used either in the hydrogen form or in the sodium form. Such resins are readily available, for example from Rohm and Haas under the "Amberlite" tradename and from Dow Chemical Co. under the "Dowex" tradename.

The ion exchange resin component is present in the formulations of the present invention at a level of from 0.05% to 10.0% by weight. The average particle size diameter of the resin ranges from 1 to 20 microns.

The particle size of the resin is important, both with respect to mode of action and comfort. Typically the average particle size of the commercially available form of the ion exchange material of choice is about 40 to 150 microns. Such particles are most conveniently reduced to a particle size range of about 1.0 to 25 microns by ball milling, according to know techniques.

Ophthalmic products are typically packaged in multidose form. Preservatives are thus required to prevent microbial contamination during use. Suitable preservatives include: polyquad, benzalkonium chloride, thimerosal, chlorobutanol, methyl paraben, propyl paraben, phenylethyl alcohol, edetate disodium, sorbic acid, Onamer M, or other agents known to those skilled in the art. Typically such preservatives are employed at a level of from 0.001% to 1.0% by weight.

The tonicity, or osmolality, of the product can be adjusted to either hypotonicity, isotonicity or hypertonicity relative to normal tears by use of conventional materials known to the art. Such tonicity agents, however, are limited to nonionic compounds and typically, when employed, range from 0.0% to 10% weight percent in the final product. Nonionic agents representatively include: mannitol, dextrose, glycerine and propyleneglycol; their presence in the final product form, however, is optional.

The compositions of the present invention can be formulated as gels, aqueous solutions, pourable liquids and anhydrous salts. The physical characteristics of the formulations will depend on the relative amounts of polymers used in the formulations. For example, aqueous solutions will typically comprise between about 5.0 to 2.0 wt. % mucomimetic polymer as described herein and about 0.1 to 3.0 wt. % polystyrene sulfonic acid polymer. Gel formulations will typically comprise 10 to 15 wt. % mucomimetic polymer and 0.1 to 8.0 wt. % polystyrene sulfonic acid polymer and pourable liquids will typically comprise 0.05 to 5.0 wt. % mucomimetic polymer and 0.1 to 5.0% polystyrene sulfonic acid polymer. The anhydrous salts are solutions, gels or pourable liquids as described above which are then lysophilized to a powder. Fillers, such as mannitol, and other materials used to facilitate the freeze/drying process can be added according to techniques known to those skilled in the art. The anhydrous salts produced in this manner can then be reconstituted into aqueous solutions or gels or pourable liquids or formulated and shaped into ocular inserts. The salts can also be combined with a nonaqueous carrier to provide for an ophthalmic ointment.

The ophthalmic formulations of the present invention are administered to the eyes as solutions or pourable liquids (eye drops), gels, and in the form of ointments and ocular inserts; the latter classifications are formulated from anhydrous salts. All such compositions are formulated to control the release of the basic active upon administration to the eye and thereby provide a sustained release effect. Typically such administration is necessary once or twice per day. The precise dosage regimen is left to the routine discretion of the clinician.

The following example is representative of formulations of the present invention useful in the sustained release of IOP lowering drugs. The formulations also provide for decreased discomfort usually associated with the use of such drugs.

EXAMPLE

The following formulation represents a preferred embodiment of the present invention.

| Ingredient | Conc (wt/v %) | Amt (grams) in 50 g Soln |
|---|---|---|
| Betaxolol hydrochloride | 0.28 | 0.14 |
| Polyacrylamidomethyl propane sulfonic acid (PAAPSA) (Aldrich) | 1.0 | 0.50 |
| Polystyrene sulfonic acid (sodium salt) (PSSA) (National Starch) | 0.1 | 0.05 |
| Mannitol | 3.6 | 1.8 |
| BAC | .01 | 0.5 ml of 1% BAC soln |
| pH | 7.0 | 7.0 |
| Osmolality Mosm/Kg | 287 | 287 |
| Purified water q.s. | 100% | 50 grams |

Procedure

The above listed amounts of PAPPSA, PSSA, betaxolol hydrochloride, mannitol and BAC were mixed together in about 70% of the water. The pH was adjusted to 7.0 with 0.1N NaOH and the solution brought to 100% with purified water.

We claim:

1. A sustained release topical ophthalmic composition useful in the treatment of glaucoma, comprising:

an amount of a beta blocker effective to control intraocular pressure;

from about 0.05 to about 15.0 percent by weight of an anionic mucomimetic polymer of the formula:

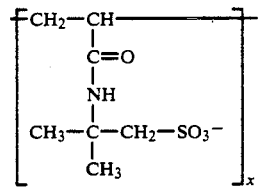

wherein x is an integer such that the polymer has a molecular weight of about 50,000 to 5,000,000; and from about 0.1 to about 8.0 percent by weight of a polystyrene sulfonic acid polymer.

2. The topical ophthalmic composition of claim 1, wherein the beta blocker is present at a concentration of between about 0.01% to about 4.0% by weight.

3. The topical ophthalmic composition of claim 2 wherein the beta blocker is selected from the group consisting of: betaxolol, timolol, acebutolol, alprenolol, atenolol, bevantolol, bucomolol, bupranolol, butidrine, bunitolol, bunolol, butocrolol, butoamine, carazolol, carteolol, exaprolol, indenolol, iprocrolol, labetolol, mepindolol, metipranolol, metaprolol, moprolol, nadolol, nifenalol, oxprenolol, pamatolol, paragolol, penbutolol, pindolol, practolol, procinolol, pronethalol, propranolol, sotalol, tazolol, tiprenolol, tolamolol, toliprolol, befunolol, esmalol, hepunolol, celiprolol, azotinolol, diacetalol, acebutolol, salbutanol and isoxaprolol.

4. The topical ophthalmic composition of claim 3, wherein the beta blocker comprises betaxolol.

5. The topical ophthalmic composition of claim 3, wherein the beta blocker comprises timolol.

6. The topical ophthalmic composition of claim 1 wherein the beta blocker comprises betaxolol at a concentration of 0.01 to 4.0 wt. % and the polystyrene sulfonic acid polymer has a molecular weight from about 10,000 to 1,600,000.

7. The sustained release topical composition of claim 1 wherein the polystyrene sulfonic acid polymer has the formula:

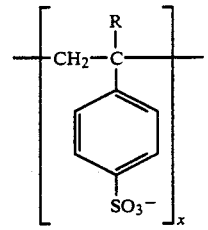

wherein: R is H or $CH_3$ and X is an integer such that the molecular weight is about 10,000 to 1,600,000.

8. The composition of claim 7 wherein R is H and the molecular weight is about 500,000 to 1,000,000.

9. A method of controlling intraocular pressure which comprises topically applying a composition of claim 1 to the affected eye.

10. The topical ophthalmic composition of claim 1 wherein the beta blocker is present at a concentration of between about 0.10 to 1.0 weight percent.

11. A sustained release topical ophthalmic composition for the treatment of glaucoma, comprising:

an amount of betaxolol effective to control intraocular pressure;

from about 0.05 to about 8.0 percent by weight of an anionic mucomimetic polymer of the formula:

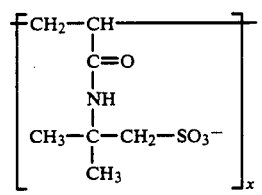

wherein x is an integer such that the polymer has a molecular weight of about 50,000 to 5,000,000; and a polystyrene sulfonic acid polymer of the formula:

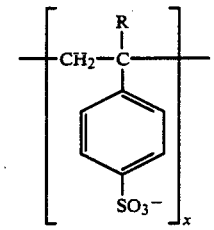

wherein: R is H or $CH_3$ and X is an integer such that the molecular weight is about 10,000 to 1,600,000.

12. The composition of claim 11 wherein the betaxolol concentration is between 0.01 and 4.0 percent by weight.

13. The composition of claim 12 wherein R is H and the molecular weight is about 500,000 to 1,000,000.

14. A method of controlling intraocular pressure which comprises topically applying a composition of claim 11 to the affected eye.

* * * * *